United States Patent
Carlsson

[19]

[11] Patent Number: 5,914,033
[45] Date of Patent: Jun. 22, 1999

[54] INSERT FOR A PRESSURE TRANSDUCER WITHIN A MEDICAL TREATMENT APPARATUS

[75] Inventor: Per-Olov Carlsson, Sosdala, Sweden

[73] Assignee: Gambro AB, Sweden

[21] Appl. No.: 08/793,036

[22] PCT Filed: Jun. 28, 1995

[86] PCT No.: PCT/SE95/00796

§ 371 Date: Apr. 25, 1997

§ 102(e) Date: Apr. 25, 1997

[87] PCT Pub. No.: WO96/05494

PCT Pub. Date: Feb. 22, 1996

[30] Foreign Application Priority Data

Aug. 15, 1994 [SE] Sweden ................................ 9402720

[51] Int. Cl.⁶ .................................................. B01D 61/30
[52] U.S. Cl. .............................. 210/90; 73/706; 73/756; 210/335; 210/435; 604/4; 604/118
[58] Field of Search ......................... 604/4–6, 118; 210/90, 85, 314, 335, 435, 446, 448, 449, 646; 73/700, 706, 756

[56] References Cited

U.S. PATENT DOCUMENTS

| | | |
|---|---|---|
| 3,371,537 | 3/1968 | Kiene . |
| 3,422,679 | 1/1969 | McGowan et al. ................. 73/706 |
| 3,818,765 | 6/1974 | Eriksen ................................ 73/706 |
| 4,227,420 | 10/1980 | Lamadrid ............................ 73/706 |
| 4,535,635 | 8/1985 | Claren et al. ....................... 73/756 |
| 4,714,464 | 12/1987 | Newton .............................. 604/118 |
| 4,838,865 | 6/1989 | Flank et al. ........................ 604/118 |
| 5,486,286 | 1/1996 | Peterson et al. ................... 210/646 |

FOREIGN PATENT DOCUMENTS

| | | |
|---|---|---|
| 0 130 441 | 1/1985 | European Pat. Off. . |
| 1134101 | 11/1968 | United Kingdom . |
| 90/06781 | 6/1990 | WIPO . |
| 92/11878 | 7/1992 | WIPO . |

*Primary Examiner*—Joseph W. Drodge
*Attorney, Agent, or Firm*—Lerner, David, Littenberg, Krumholz & Mentlik

[57] ABSTRACT

Removable inserts are disclosed for positioning within a dialysis machine in order to connect a pressure transducer to external apparatus such as a drip chamber. The removable insert comprises a cup-shaped container adapted to be disposed within the dialysis machine with its open end aligned with the front face of the dialysis machine, a cover to cover the open end of the container, the cover including an orifice, a tube extending from the closed end of the cup-shaped container for communication with the pressure transducer, a filter positioned within the container, and a coupler for coupling the tube with the orifice in the cover with the filter interposed therebetween so that the pressure associated with the drip chamber can be monitored by the pressure transducer.

12 Claims, 2 Drawing Sheets

INSERT FOR A PRESSURE TRANSDUCER WITHIN A MEDICAL TREATMENT APPARATUS

FIELD OF THE INVENTION

The present invention relates to an insert for a pressure transducer located in a medical treatment apparatus, such as a dialysis machine. The pressure transducer is intended for connection to an apparatus located outside the machine, such as a drip chamber in a tube-set which is used with dialysis performed by the dialysis machine.

BACKGROUND OF THE INVENTION

In dialysis procedurers, blood is taken out of the body in an extra-corporeal closed circuit and passes on one side of a membrane located in a dialyser. A dialysis solution circulates on the other side of the membrane. A dialysis machine contains the necessary pumps and other equipment for performing and monitoring the dialysis process, which can be hemodialysis, hemodiafiltration and/or hemo-filtration.

In order to ensure that no dangerous conditions arise for the patient, the dialysis machine is provided with several pressure transducers, which can be arranged at different positions along the extra-corporeal blood circuit. Examples of the use of pressure transducers in such systems are disclosed European Patent Nos. 130,441 and 134,436, which show cassettes with integrated connections to such pressure transducers positioned in the dialysis machine.

Apart from the pressure transducers which are disclosed in these patents, the pressure transducers themselves are intended for connection to tubes. Luer-couplings of the male type are thus mounted on the front of the dialysis machine. Each luer-coupling is connected to a pressure transducer inside the machine by means of a tube, and the pressure transducer converts the pressure in the tube into an electric signal. This pressure transducer is normally mounted on a circuit board. The pressure at the orifice of the luer-coupling is transmitted through the tube to the pressure transducer, with air in the tube acting as the pressure medium. The tube between the luer-coupling and the pressure transducer is provided with a filter, the function of which is to prevent fluid, particularly blood, being able to reach the pressure transducer. Thus, the filter only allows air to pass therethrough.

The apparatus, of which the pressure is to be sensed, is connected to the luer-coupling. An example of such an apparatus is a drip chamber or air separator positioned on the venus side of a tube-set. A tube leeads from the upper end of the drip chamber, and the tube is provided with a blood filter and a luer-coupling of the female type. This luer-coupling of the female type can be connected with the luer-coupling of the male type which is positioned on the front of the dialysis machine so that the machine can monitor the venous pressure in the drip chamber.

By arranging a blood filter in the tube from the drip chamber it is ensured that blood is not able to reach the luer-coupling positioned on the front of the dialysis machine. As a means of double safety the aforementioned blood filter is positioned in the tube between the luer-coupling and the pressure transducer within the machine.

When servicing dialysis machines of the type designated as in GAMBRO AK 100 we have found that it is inevitable that in some cases blood passes to the male type luer-coupling and into the interior of the machine. In principal this should not be possible, since the outer blood filter should prevent such blood leakage.

Cleaning of a machine which has been subjected to such blood leakage is relatively complicated, and has to be carried out by specially trained service personnel. In this case the tube positioned in the machine is replaced and the luer-coupling in the machine is cleaned. If the luer-coupling cannot be cleaned this must be replaced as well.

Hopefully, the blood filter within the machine has remained intact and, if so, the pressure transducer can be retained. Otherwise, even this must be replaced, which is very expensive.

It is presumed that many of the discovered cases of blood leakage are caused by the fact that the dialysis machine is used with tube-sets of a basic type which lack separate blood filters. However, with the provision of double safety measures, the dialysis machine can, despite this, be saved from the necessity for costly repairs.

When handling blood in an extra-corporeal closed circuit, measures must be taken to minimize the risk of infection, particularly with hepatitis and AIDS. Blood which leaks into the machine and remains there can be a source of infection for the next patient, and, therefore, a machine where leakage has occurred must be attended to immediately.

The insert according to the present invention can also be used in connection with the sensing of pressure in circuits which contain fluids other than blood, such as in machines intended for other medical uses, for example in connection with infusion or peritoneal dialysis.

SUMMARY OF THE INVENTION

In accordance with the present invention, these and other objects have now been accomplished by the invention of a removable insert for positioning within a medical treatment apparatus having a front face in order to connect a pressure transducer to external apparatus having an associated pressure to be monitored by the pressure transducer. The apparatus comprises a container having an open end and a substantially closed end, the container adapted to be disposed within the medical treatment apparatus when the open end of the container is substantially aligned with the front face of the medical treatment apparatus, a cover member for covering the open end of the container, the cover member including an orifice, a tube member extending from the substantially closed end of the container for communication with the pressure transducer, a filter positioned in the container, and coupling means for coupling the tube member with the orifice in the cover member with the filter interposed therebetween, whereby the pressure associated with the external apparatus can be monitored by the pressure transducer. In accordance with a preferred embodiment, the medical treatment apparatus comprises a dialysis machine.

In accordance with one embodiment of the removable insert of the present invention, the container is substantially cup shaped.

In accordance with another embodiment of the removable insert of the present invention, the removable insert is adapted to connect the pressure transducer to external apparatus comprising a drip chamber.

In accordance with another embodiment of the removable insert of the present invention, the tube member extends to the external surface of the container and includes a coupling for the pressure transducer. In a preferred embodiment, the removable insert includes the pressure transducer affixed to the coupling.

In accordance with another embodiment of the removable insert of the present invention, the tube member includes a tube connection located externally of the container, whereby the tube connection can be connected to a remote pressure transducer.

In accordance with another embodiment of the removable insert of the present invention, the cover member includes a coupler for coupling the coupling means to the external apparatus. Preferably, the coupling comprises a male luer coupler.

In accordance with another embodiment of the removable insert of the present invention, the coupling means includes a relatively thick walled tube including an inner lumen dimensioned to receive a connector inserted through the orifice in the cover member.

In accordance with another embodiment of the removable insert of the present invention, the removable insert includes a secondary filter disposed between the container and the pressure transducer.

In accordance with another embodiment of the removable insert of the present invention, the tube member is concentrically disposed within the substantially closed end of the container and extends through the wall of the closed end of the container for connection to the pressure transducer.

The object of the present invention is to thus provide an insert for a pressure transducer in connection with a dialysis machine or the like. The insert contains a filter unit which provides for the double safety discussed above. By placing the filter unit in the insert a simple replacement of the filter unit is possible, without the need for costly intervention of service technicians.

A further object of the present invention is to provide an insert for a pressure transducer which contains a filter unit, such that at the same time an additional filter unit can be provided within the machine in order to achieve triple safety.

An additional object of the present invention is to provide an insert for a pressure transducer provided with a cover. The cover contains a luer-coupling of the male type for connection to previously used apparatus provided with a luer-coupling of the female type.

BRIEF DESCRIPTION OF THE DRAWINGS

The invention will now be described in more detail below with reference to the embodiments of the invention depicted in the drawings, as follows.

DETAILED DESCRIPTION

Figure 1:
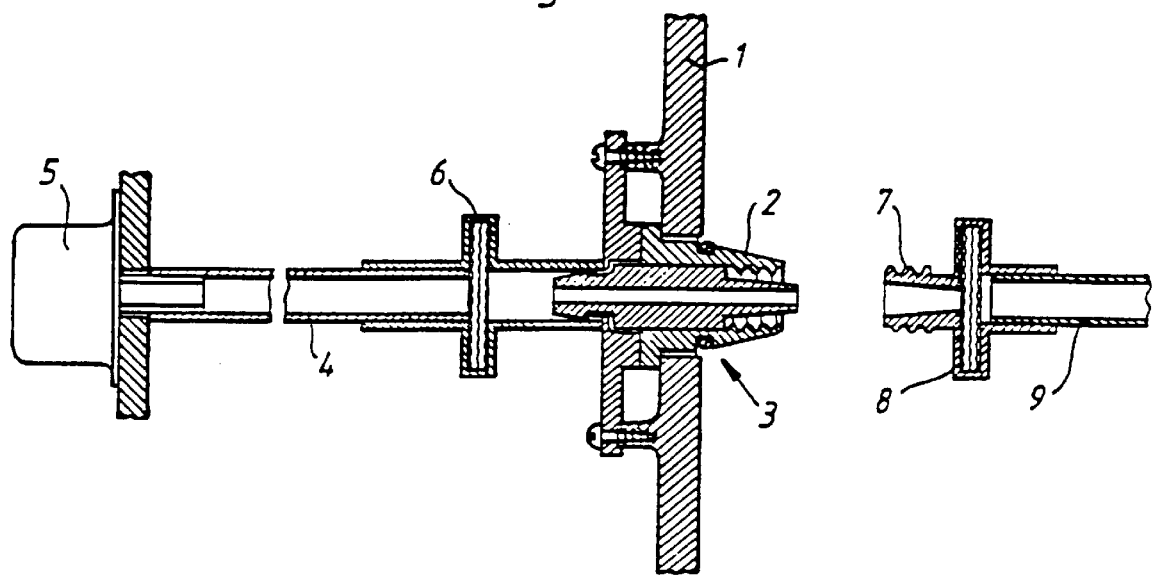
FIG. 1 is a side, elevational, cross-sectional view of a pressure sensor with a luer-coupling according to the state of the art.

Referring to the Figures, in which like reference numerals refer to like elements thereof, FIG. 1 shows a cross-sectional view of a pressure transducer according to the state of the art, such as that presently utilized on the dialysis machine known as GAMBRO AK 100.

The dialysis machine is shown only in the form of a front panel 1. A luer-coupling 2 of the male-type extends through the front. The coupling is attached to the front 1 by means of a holder 3. Within the dialysis machine, to the left of the front in FIG. 1, the luer-coupling 2 is connected to a pressure transducer 5 by means of a tube 4 containing a blood filter 6.

The pressure transducer 5 is mounted on an electric circuit board which is normally located at a distance from the front 1.

A blood filter 6 is arranged on the tube 4. The blood filter 6 is a disc filter with a pore-size of about 0.2 mm. The membrane of the filter itself is manufactured from a hydrophobic material such as PTFE (teflon). In this way the membrane allows air to pass through it but cannot allow fluid, particularly blood, to pass therethrough. The membrane further forms a barrier for particles larger than about 0.2 mm, such as bacteria and most viruses. Other types of filters can of course be used.

The filter can be positioned anywhere on the tube, but is preferably arranged as close to the front 1 as possible, i.e. immediately behind the luer-coupling 2, as shown in FIG. 1.

The apparatus, of which the pressure is to be measured, is coupled to the luer-coupling 2 by means of a tube 9 which ends in a luer-coupling 7 of the female type. In the embodiment shown in FIG. 1, the luer-coupling 7 is integrated with a blood filter of the disc type 8. The disc filter is of a known construction, and can be the same filter as the filter 6 within the apparatus. The apparatus in question is connected to the filter 8 by means of the tube 9. The apparatus can be a drip chamber in a tube-set for the extra-corporeal transport of blood in connection with hemodialysis. The venous pressure is thus measured in the drip chamber.

If a simpler tube-set, which has no filter 11, is used, there is a risk that blood will pass through the luer-coupling 7 to the luer-coupling 2 and further into the inside of the machine into tube 4 and up to the blood filter 6 positioned therein. In order to clean a machine contaminated in this way, the casing of the machine has to be opened and the tube 4 containing the filter 6 replaced, as well as the luer-coupling 2 being replaced where necessary.

In order to facilitate such a replacement of the inner blood filter it is, in accordance with the present invention, placed in a separate insert mounted on the front of the machine. Such a device is shown in more detail in FIG. 2.

Figure 2:
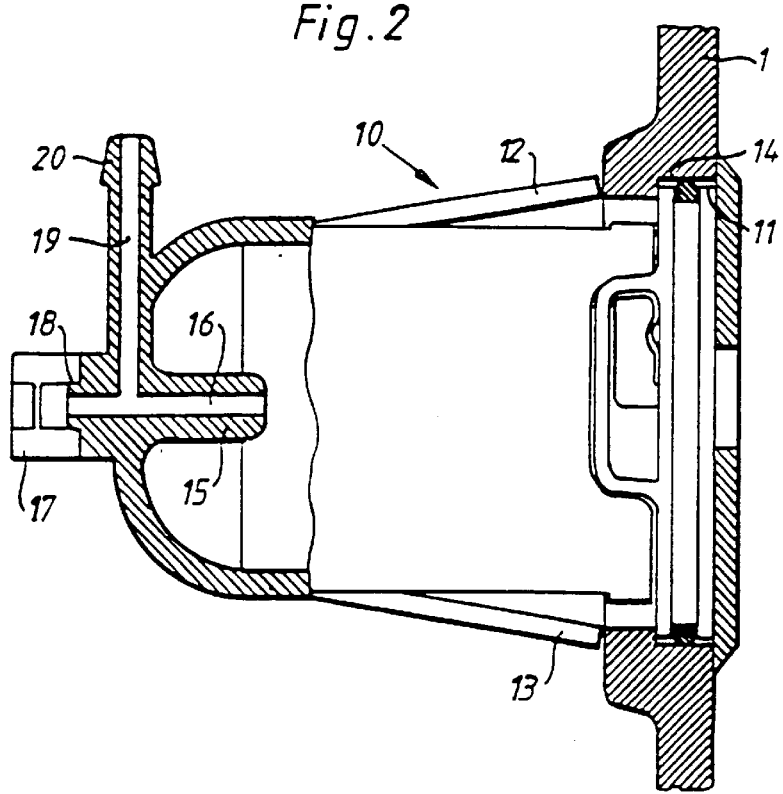
FIG. 2 is a side, elevational, cross-sectional view, of an insert according to the present invention.

FIG. 2 shows the front 1 of the machine provided with an insert according to the present invention. The insert consists of a cup-shaped container 10 with an outer flange 11 which is sealingly located in a hole 14 in the front 1. The insert is maintained therein by means of hooks 12 and 13 which grip behind the front 1 when the insert 10 is inserted through a hole 14 in the front.

At its bottom, to the left in FIG. 2, the container is provided with an integral horizontal tube 15 which is concentrically positioned in the container 10. The tube 15 is provided with a through-hole 16 which is connected to a holder 17 for a pressure transducer (see FIG. 3) by means of a projecting stud 18. The hole 16 is connected with a transverse hole 19 positioned in a tube-coupling 20. The function of this hole 19 will be explained in more detail below.

Figure 3:
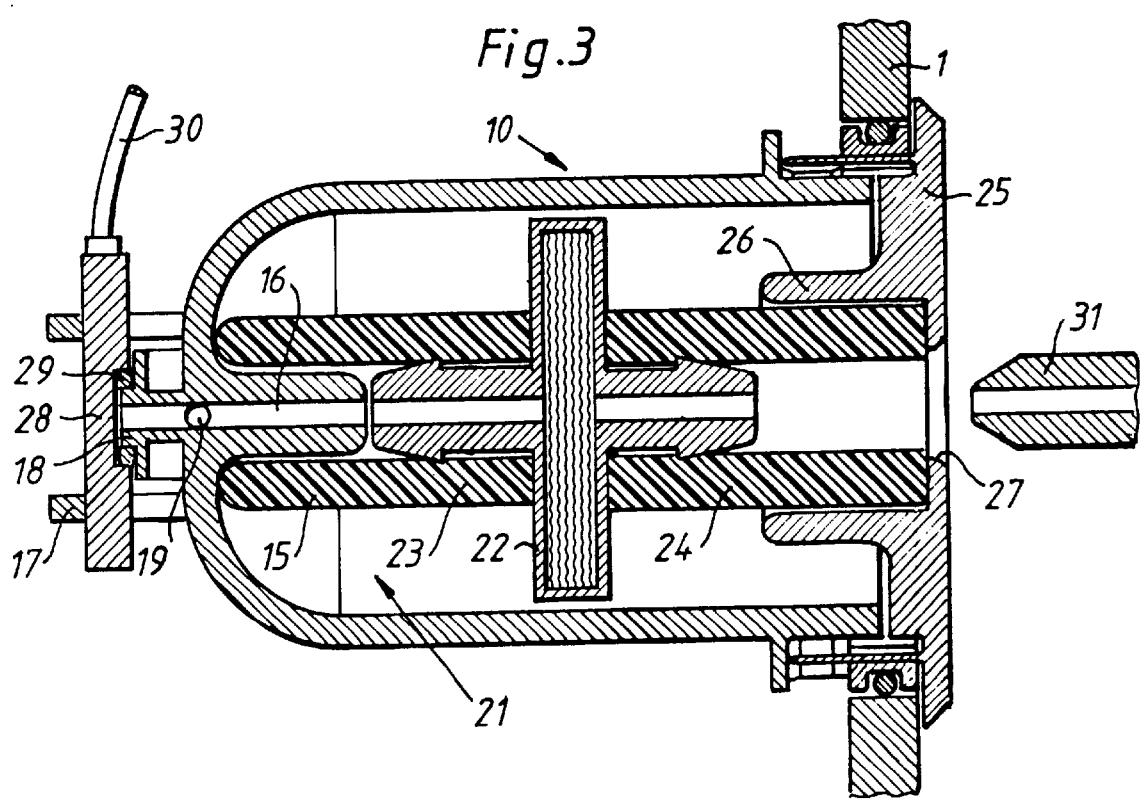
FIG. 3 is a side, elevational, cross-sectional view of the insert according to FIG. 2, provided with a filter unit according to the present invention.

The orifice of the insert 10, to the right in FIG. 2, is covered by a cover which is shown in more detail in FIG. 3.

FIG. 3 shows the insert 10 according to a preferred embodiment of the invention. A filter unit 21 is mounted on the tube 15, the filter unit consisting of a blood filter 22 and thick-walled tube pieces, 23 and 24, arranged on either side of the filter. The tube piece 23 connects the filter 22 with the tube 15. The tube piece 24 cooperates with the other end of the blood filter and extends to the right in FIG. 3 up to a cover 25, which covers the open end of the insert 10. The cover 25 has a cylindrical portion 26 which extends into the insert 10 and cooperates with the tube piece 24. The cover 25 is additionally provided with a hole 27. The hole 27 is positioned just in front of the tube piece 24 so that the outer end of the tube piece is accessible from the outside through the hole.

A pressure transducer 28 located in the holder 17 is shown to the left of the insert 10, as seen in FIG. 3. The pressure-sensitive surface of the pressure transducer is positioned directly in front of the hole 16 in the tube 15 and against the projecting stud 18. A seal 29 ensures that the stud 18 is sealed with respect to the pressure transducer 28. The pressure transducer 28 is electrically connected with a circuit board positioned at a distance from the insert 10 by means of conduits 30. The conduits and the electrical contacts are well insulated in order to be properly protected. The pressure transducer 28 is of a conventional construction and comprises, for example, a piezoelectric crystal as the active element. The pressure transducer 28 can sense over-pressure as well as under-pressure with respect to the surrounding atmosphere.

The insert according to FIG. 3 is intended to cooperate with a drip chamber having a specially shaped head which is provided with an integrated blood filter as well as an outlet connection stub 31, of which only the connection stub 31 is shown in FIG. 3. The exact design of the drip chamber head is disclosed in the International patent application no. . . . (corresponding to Swedish Patent Application No. 94.02721-6) filed concurrently herewith, to which reference is made.

The drip chamber is attached at the front 1 by means of holding means intended therefor, which are so placed that the stub 31 is positioned directly opposite the insert 10. When putting the drip chamber into place the stub 31 passes through the hole 27 in the cover 25 into cooperation with the tube piece 24 which seals against the stub 31. In this way a sealed connection is achieved between the upper part of the drip chamber and the pressure transducer 28 through the blood filter 22 and the blood filter integrated into the drip chamber head. In this way double safety is obtained.

If, in spite of this, leakage of blood should occur through the blood filter integrated in the drip chamber head, the blood reaches no further than the blood filter 22 in the insert. When any such leakage is noticed, the cover 25 is removed and the insert 21 can be readily replaced. This is a relatively simple operation and can be carried out without interfering with the machine itself, and without the assistance of service-personnel.

When using the insert according to the present invention in connection with a drip chamber, an over-pressure is present in the connection stub 31 and the hole 16. It is desirable to be able to adjust the level in the drip chamber by regulating the amount of air contained in the drip chamber. This occurs by means of the aforementioned transverse hole 19 and tube coupling 20 (only the hole 19 being visible in FIG. 3). The tube coupling 20 and the hole 19 are connected to a pump, by means of which air can pass through the hole 16 to or from the drip chamber, whereby the level in the drip chamber is adjusted.

If this function is not required, the transverse hole 19 (see FIG. 2) can be closed with a cover. Alternatively, two embodiments of the insert 10 are made, where the hole 19 is closed in one of them. The latter embodiment can for example be used in connection with a pressure transducer for arterial pressure.

The insert 10 according to the present invention can also be adapted for use together with a pressure transducer 5 according to the embodiment in FIG. 1. In this connection, the holder 17 is replaced by a tube coupling 32, such as shown in FIG. 4, which by means of an air tube 4 is connected with the pressure transducer 5.

Figure 4:
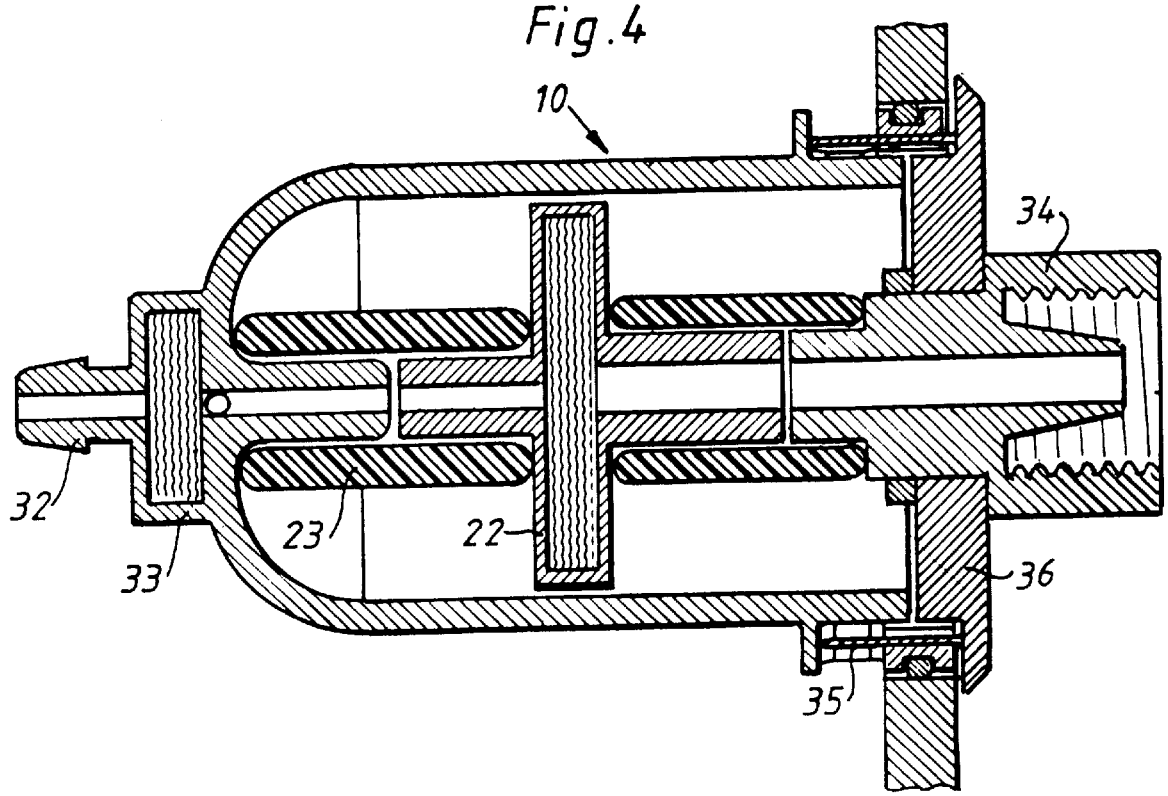
FIG. 4 is a side, elevational, cross-sectional view similar to FIG. 3, showing an alternative embodiment of the insert according to the present invention.

In order to obtain triple safety, the tube coupling 32 can be provided with an integrated blood filter 33, such as shown in FIG. 4. This blood filter can, however, normally be omitted.

FIG. 4 additionally shows the insert 10 provided with a luer-coupling of the male type 34 corresponding to the coupling 2 in FIG. 1. Once provided with this coupling 34, the insert 10 can be used for blood tubes or tube-sets according to known technology.

The luer-coupling 34 of the male type is fixed to a cover 36 or formed in one piece with the cover 36 on the insert 10. The cover 36 is fixed to the front 1 and the insert by means of a bayonet coupling 35. The luer-coupling 34 is thus fixed with respect to the front of the machine. The insert 10 according to the present invention is provided with a blood filter 22 similar to that shown in FIG. 3. By connection to a luer 7 of the female type according to FIG. 1, the same function as in FIG. 1 is achieved.

By using both the filter 22 and filter 33, an outer blood filter 8 can be omitted in certain applications, if such is desired.

It is possible to manufacture the cover 36, the coupling 34 as well as the blood filter 22 in a single piece, whereby this complete component is replaced in the event of blood leakage.

Instead of coupling the pressure transducer 28 to a circuit board positioned at a distance by means of conduits 30, the circuit board can be positioned at the bottom of the insert 10 in connection with the pressure transducer.

The invention has been described above with reference to preferred embodiments of the invention. These embodiments can be modified by a skilled man in many ways and such modifications which are obvious for a skilled man are intended to be encompassed within the scope of the invention. The various components described, can be combined in different ways to those shown in the drawings.

I claim:

1. A removable insert for positioning within a medical treatment apparatus having a front face in order to connect a pressure transducer to external apparatus with an associated pressure to be monitored by said pressure transducer, said removable insert comprising a container having an open end and a substantially closed end, said container adapted to be disposed within said medical treatment apparatus when said open end of said container is substantially aligned with said front face of said medical treatment apparatus, a cover member for covering said open end of said container, said cover member including an orifice, a tube member extending from said substantially closed end of said container for communication with said pressure transducer, a filter positioned with said container, and coupling means for coupling said tube member with said orifice in said cover member with said filter interposed therebetween whereby said pressure associated with said external apparatus can be monitored by said pressure transducer.

2. The removable insert of claim 1 wherein said medical treatment apparatus comprises a dialysis machine.

3. The removable insert of claim 1 wherein said container is substantially cup-shaped.

4. The removable insert of claim 1 adapted to connect said pressure transducer to external apparatus comprising a drip chamber.

5. The removable insert of claim 1 wherein said container includes an internal surface and an external surface, and wherein said tube member extends to the external surface of said closed end of said container and includes a coupling for said pressure transducer.

6. The removable insert of claim 5 including said pressure transducer affixed to said coupling.

7. The removable insert of claim 1 wherein said tube member includes a tube connection located externally of said container, whereby said tube connection can be connected to a remote pressure transducer.

8. The removable insert of claim 1 wherein said cover member includes a coupler for coupling said coupling means to said external apparatus.

9. The removable insert of claim 8 wherein said coupler comprises a male luer-coupler.

10. The removable insert of claim 1 including a secondary filter disposed between said container and said pressure transducer.

11. The removable insert of claim 1 wherein said tube member is concentrically disposed within said substantially closed end of said container and extends through a wall of said closed end of said container for connection to said pressure transducer.

12. A removable insert for positioning within a medical treatment apparatus having a front face in order to connect a pressure transducer to external apparatus with an associated pressure to be monitored by said pressure transducer, said removable insert comprising a container having an open end and a substantially closed end, said container adapted to be disposed within said medical treatment apparatus when said open end of said container is substantially aligned with said front face of said medical treatment apparatus, a cover member for covering said open end of said container, said cover member including an orifice, a tube member extending from said substantially closed end of said container for communication with said pressure transducer, a filter positioned with said container, and coupling means for coupling said tube member with said orifice in said cover member with said filter interposed therebetween whereby said pressure associated with said external apparatus can be monitored by said pressure transducer, said coupling means including a relatively thick walled tube including an inner lumen dimensioned to receive a connector inserted through said orifice in said cover member.

* * * * *